United States Patent [19]

Child

[11] 4,308,859
[45] Jan. 5, 1982

[54] METHOD OF INHIBITING MASTITIS IN BOVINE ANIMALS

[75] Inventor: Francis W. Child, Eagle Bend, Minn.

[73] Assignee: Child Laboratories Inc., Eagle Bend, Minn.

[21] Appl. No.: 62,707

[22] Filed: Aug. 1, 1979

[51] Int. Cl.³ .............................................. A61B 19/00
[52] U.S. Cl. .................................. 128/1 R; 128/264; 128/788
[58] Field of Search ............ 128/264, 130, 788, 260.1; 119/14.02, 14.19, 14.21, 14.22

[56] References Cited

U.S. PATENT DOCUMENTS

| | | | |
|---|---|---|---|
| 8,736 | 3/1835 | Harrington | 128/788 |
| 876,775 | 1/1908 | Crittenden | 128/343 |
| 1,042,624 | 10/1912 | Magoner | 128/788 |
| 1,661,494 | 3/1928 | Neilsen | 128/349 R |
| 1,995,051 | 3/1935 | Benson | 119/14.21 |
| 2,069,112 | 1/1937 | Oppenheim | 128/409 |
| 2,121,875 | 6/1938 | Kruse et al. | 204/24 |
| 2,276,623 | 3/1942 | Meiman | 433/32 |
| 2,355,231 | 8/1944 | Moore | 128/172.1 |
| 2,547,758 | 4/1951 | Keeling | 128/349 |
| 2,655,922 | 10/1955 | Knappwost | 128/409 |
| 3,019,787 | 2/1962 | Simmons | 128/172.1 |
| 3,385,300 | 5/1968 | Holter | 128/348 |
| 3,964,477 | 6/1976 | Ellis et al. | 128/172.1 |
| 4,027,393 | 6/1977 | Ellis et al. | 433/173 |
| 4,126,937 | 11/1978 | Ellis et al. | 433/228 |
| 4,202,329 | 5/1980 | Kortum | 128/131 X |

OTHER PUBLICATIONS

Silver by C. M. Gruber, Ph.D, M.D., The Cyclopedia of Medicine, Surgery Specialties, vol. XII, p. 693.
"Germicides, Fungicides, and Ectoparasiticides," by Louis S. Goodman, M.A., M.D. & Alfred Gilman, Ph.D, The Pharmacological Basis of Therapeutics, p. 1105.
"Silver-New Magic in Medicine," Sci/Di, Mar. 1978, pp. 58-60.
Aadr Abstracts, 1977, No. 572, p. B195, "Theoretical Biophysics", Biophysical Journal, vol. 25, p. 217a.
Agricultural Research, U.S. Dept. of Agriculture, Sep. 1979, "New Loop in Mastitis Prevention", p. 35.
Wisconsin Agriculturist, Nov. 24 1979, "Plastic Loop May Help Battle Mastistis", p. 17.

Primary Examiner—Stephen C. Pellegrino
Attorney, Agent, or Firm—Burd, Bartz & Gutenkauf

[57] ABSTRACT

A method and instrument for placing an implant in the teat duct and udder of an animal, as a milk cow. The instrument has an elongated tubular member having a passge accommodating the implant. The tubular member is adapted to be inserted into the milk duct through the discharge end thereof. A head having finger gripping ears is attached to the tubular member. The implant is moved from the passage with a piston connected to a rod extended through the head. A head engaging member secured to the rod is used in cooperation with the ears to apply force to the rod to move the piston in the passage to move the implant into the teat duct and udder. The implant has a core of an elongated flexible plastic string. A plurality of bands are clamped about the core. Alternate bands are coated with a first metal, as silver. The remaining bands are coated with a second metal, as gold. All of the bands may be coated with the same metal, such as silver. The implant includes a capsule implant containing material that reacts with the silver to produce silver ions which have advantageous antibacterial effects.

4 Claims, 8 Drawing Figures

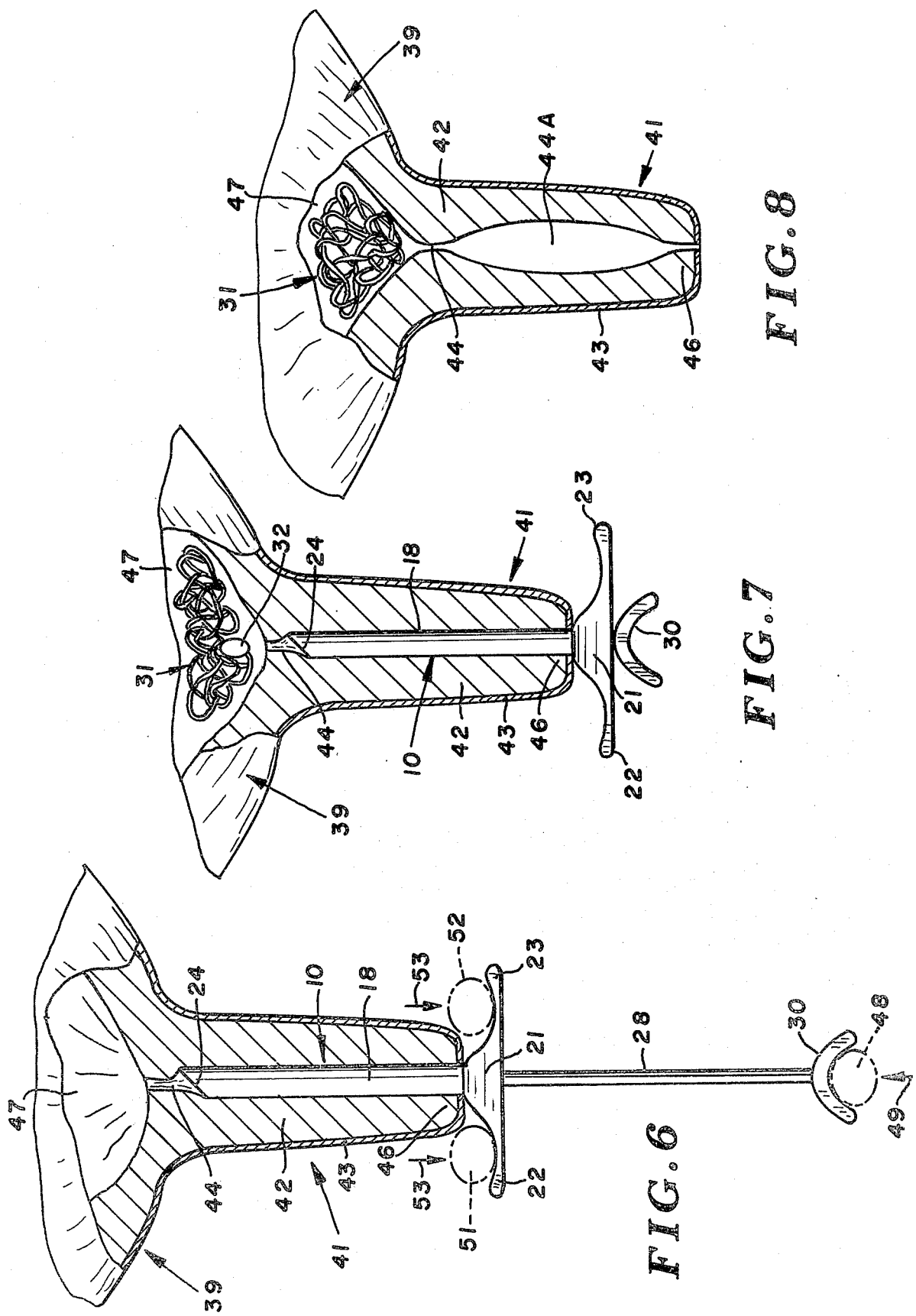

METHOD OF INHIBITING MASTITIS IN BOVINE ANIMALS

SUMMARY OF INVENTION

The invention relates to an instrument and method for placing an implant into the teat duct and udder of an animal, as a milk cow. The instrument is a hand-operated dispenser which places the implant in the teat duct and dispenses the implant into the teat duct and udder. The instrument has an elongated cylindrical tubular member having a passage for accommodating the implant. A head is attached to a rear portion of the tubular member. Finger grips secured to the head are used to facilitate the insertion of the tubular member into the milk duct and the dispensing of the implant into the milk duct and udder. A movable piston is located in the passage. A piston rod secured to the piston is used to move the piston in the passage and thereby force the implant from the passage. A curved member attached to the piston rod functions to accommodate the thumb so that the instrument is hand-operated with two fingers and the thumb.

The implant has an elongated flexible plastic core carrying a plurality of metal bands. Each band has a metal coating which releases metal ions in response to an electrical power providing effective micro-organism control, including bacterial action and germicidal action. The metal is preferably silver. Other metals, as gold, aluminum, copper, zinc, and compounds as silver-zinc-allantoinate, and silver sulfadiazine and like metals, and metal alloys which liberate metal ions, can be used. The alternate segments of the core can have dissimilar metals which produce a galvonic action which causes release of metal ions. The implant can be a capsule implant which, when dispensed into the udder, will dissolve in the udder and release a chemical or one or more materials. The chemical can be a sulfur compound which reacts with silver to enhance the liberation of silver ions.

The dispensing instrument is packaged in an envelope. The envelope comprises two sheet members that are adhesively sealed together to maintain the dispenser and implant located in the dispenser in a sterile condition. The envelope sheet members are separated to expose the instrument prior to its insertion into the milk duct of a teat. The instrument is an economical device that can be made of low-cost plastic material. After use, the instrument is disposed of to prevent the contamination of other teats. The instrument can be used by veterinarians, as well as animal husbandrists, to control and treat mastitis.

IN THE DRAWINGS

FIG. 6 is an elevational view of the instrument inserted into the milk duct of a cow's teat prior to the dispensing of the implant into the milk duct and udder;

FIG. 7 is a view similar to FIG. 6 showing the dispensing instrument in the dispensed position with the implant located in the udder; and FIG. 8 is a sectional view of the udder and teat with the implant located in the udder and the dispensing instrument removed from the teat.

DESCRIPTION OF PREFERRED EMBODIMENT

Figure 1:
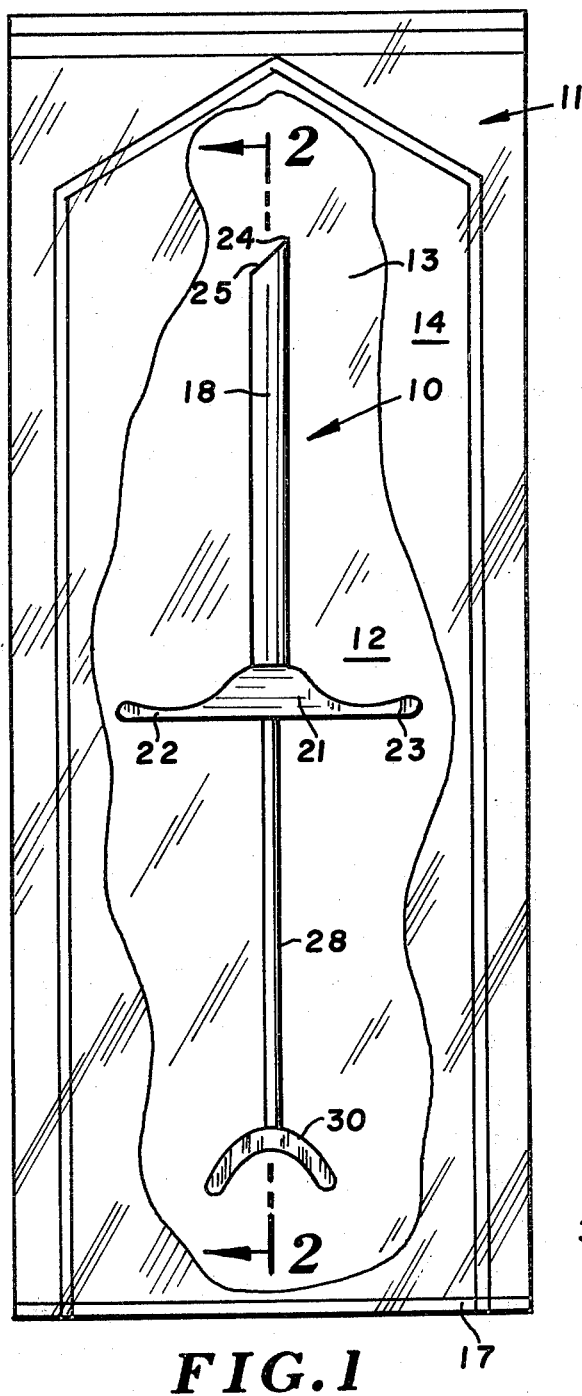
FIG. 1 is a side elevational view of the dispensing instrument of the invention located within a shipping envelope partly broken away to show the instrument.

Referring to FIG. 1, there is shown a dispensing instrument of the invention indicated generally at 10 located within an envelope 11. Envelope 11 has an elongated chamber 12 formed by side-by-side sheet members 13 and 14. Sheet members 13 and 14 are flexible plastic sheets. The sides and top of sheet members 13 and 14 are releasably secured together with parallel seals 16. Seals 16 are continuous beads of adhesive material which can be separated from one sheet member to open the envelope. This is done by pulling the upper ends of sheet members 13 and 14 apart. A transverse seal 17, such as a heat seam, secures the bottom end of the envelope thereby hermetically sealing the dispensing instrument 10 in the envelope. Chamber 12 can accommodate disinfectant solutions. Envelope 11 is used to store and transport dispensing instrument 10 in a sterile condition. The envelope 11 can be used as a bag to disinfect the teat with a disinfectant before the instrument is inserted into the milk duct of the teat.

Dispensing instrument 10 has an elongated tubular finger, probe or tubular member 18 surrounding an elongated chamber or bore 19. Member 18 is a linear or straight cylindrical member or tube having an inside cylindrical wall surrounding chamber 19. Chamber 19 has a uniform diameter throughout its length. An enlarged head 21 is integral with the rear end of member 18. The forward side of head 21 has a convex shape which functions as a stop indicating the full in position of member 18. Head 21 has outwardly directed ears 22 and 23 which serve as finger engaging members to facilitate the installation or insertion of tubular member 18 into the milk duct of a teat of an animal. The forward end of tubular member 18 has a tip 24 surrounding a discharge opening 26 in direct communication with chamber 19. Tip 24 is part of an inclined forward end 25. The shape of end 25 minimizes resistance to insertion of member 18 into the milk duct of a teat.

A movable plunger or piston 27 is located in chamber 19. Piston 27 is connected to a linear rod 28 that extends rearwardly from piston 27 through a hole 29 in head 21. The outer end of rod 28 is integral with a thumb engaging member 30. Member 30 has an arcuate or generally C-shape to accommodate the thumb of the user and to locate the thumb in general alignment with rod 28 so that a linear force can be applied to rod 28 to move piston 27 up into elongated chamber 19.

Figure 2:
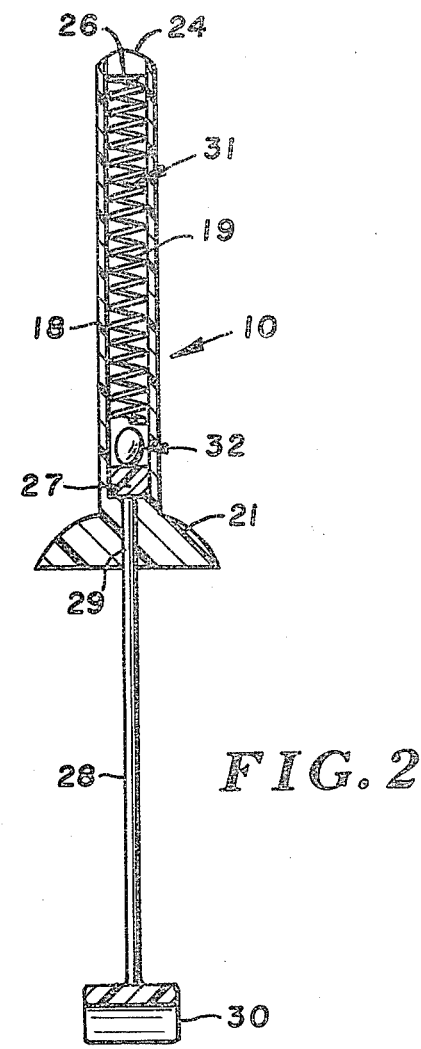
FIG. 2 is a sectional view of the dispensing instrument taken along the line 2—2 of FIG. 1.

An implant 31 is located in chamber 19. As shown in FIG. 2, a second implant 32 is located above piston 27 and below implant 31. Implant 32 is a capsule implant containing antibacterial and virus compounds or solutions that are to be injected into the udder of a cow to treat mastitis and other infections. The capsule has a cover or sheet of material that dissolves in the udder. A sulfur compound can be stored in the capsule. For example, dimethyl sulfoxide can be introduced into the teat duct and udder with capsule implant 32. The material in implant 32, when released in the udder, can be of the type that reacts with implant 31 to produce antibacterial and virus agents, compounds or chemicals. Implant 32 can be several capsules. Each capsule can have different material.

Figure 5:
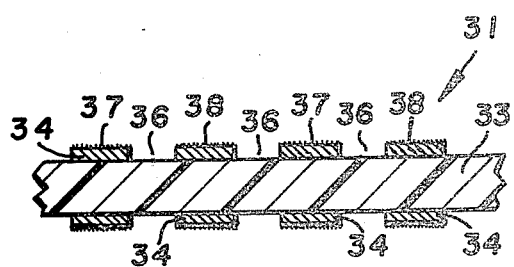
FIG. 5 is a sectional view taken along the line 5—5 of FIG. 3.
Figure 3:
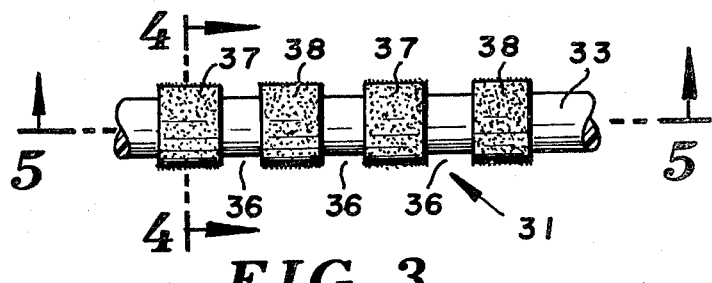
FIG. 3 is a plan view of a portion of the implant.
Figure 4:
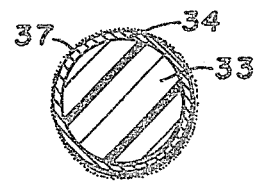
FIG. 4 is an enlarged sectional view taken along the line 4—4 of FIG. 3.

Referring to FIGS. 3 to 5, implant 31 has a core 33 comprising an elongated flexible string of plastic material, such as Selastic. The plastic material is biologically inert and compatible with body tissue and fluids in the udder. A plurality of metal bands 34 are located about core 33 and clamped onto the core. Preferably, bands 34 are stainless steel and have a length about equal to the diameter of the core. Adjacent bands 34 are longitudinally spaced from each other to permit the flexible core 33 to bend and stretch to conform to the milk duct and cavities in the udder. The space between adjacent bands is about equal to the diameter of core 33. Core 33 has a relatively small diameter, such as 1 to 10 mm. The size of core 33 and length of bands 34 and spacing between adjacent bands 34 can vary.

Alternate bands 34 are coated with a layer of silver 37. The remaining bands 34 are covered with a coating or layer of gold 38. The silver and gold can be vacuum deposited onto the bands by a sputtering process. As an alternate structure, the spaced silver and gold layers can be deposited directly onto the elastic core thereby eliminating metal bands 34. As another alternative, each band 34 can be coated with a segment of silver and a segment of gold. The silver and gold metals are used by way of an example. Other types of metals can be deposited onto the bands or core. Metals, as aluminum, copper, and zinc, metal alloys, and materials as silver-zinc-allantoinate, silver sulfadiazine, and the like, may be used. All of the bands can be coated with silver. The entire implant 31 can be a silver or silver alloy wire. The dissimilar metals, when located in the body or udder fluids, causes galvonic action which produces an electric current that liberates metal ions. When silver is used, silver ions flow through the body or udder tissue producing beneficial antiseptic results and bactericidal action and germicidal action. Other metal ions produce similar results. Implant 32 can contain a sulfur compound which reacts with the silver to produce an electric current causing silver ions to form and move with the current.

Referring to FIG. 6, the udder indicated generally at 39 has a teat 41. The other teats of the udder are not shown. A milk duct 44 extends longitudinally through the teat from a milk collecting cavity or cistern 47 at the base of the udder to a discharge opening at the end of the teat. The discharge opening is closed with a sphincter muscle 46.

Envelope 11 is opened by separating sheet members 13 and 14. This exposes the forward end 24 of finger 18. Finger 18 is placed up or inserted into milk duct 44 with the tip or forward end 24 located adjacent the exit of the cavity 47. The hand fingers engageable with envelope 11 and head 21 are used to insert the finger 18 into milk duct 44. Rod 28 extends downwardly from head 21 locating piston 27 in the base of passage 19. Implants 31 and 32 have been previously loaded in the passage 19, as shown in FIG. 2.

The thumb 48 and first and second fingers 51 and 52 are used to dispense implants 31 and 32 into the udder cavity 47. As shown in FIG. 6, thumb 48 is placed on the C-shaped member 30 at the end of rod 28. The first and second fingers are placed over the ears 22 and 23. The thumb is moved toward the head 21 by applying pressure in the direction of the arrow 48. The hand fingers 51 and 52 apply pressure in the direction of the arrows 53 to maintain finger 18 in milk duct 44. Thumb 48 forces the rod 28 into head 21. The piston 27 moves implants 31 and 32 out of passage 19 into udder cavity 47. Near the end of the stroke the piston 27 moves implant 32 into the upper end of the milk duct adjacent cavity 47. Implant 32 can be moved into cavity 47 by moving finger 18 upwardly. As shown in FIG. 7, rod 28 is moved to head 21 dispensing implants 31 and 32 into cavity 47. The dispensing instrument 10 is withdrawn from teat 41 by pulling on ears 22 and 23. Instrument 10, being a low cost item, is disposed of in a sanitary manner.

FIG. 8 shows the udder 39 and teat 41 with instrument 10 removed. When finger 18 is removed from duct 44, the duct 44 returns to its natural condition with an enlarged teat chamber 44A located between the upper portion of the teat and the sphincter muscle 46. Implant 31 is located in the udder cavity 47. Implant 32 has dissolved thereby releasing the material therein into the udder. The material in implant 32, such as sulfur compound, forms a slight acid condition in the udder. The acid reacts with the silver and gold to produce an electrical current. The electrical current liberates silver ions. The silver ions disperse, penetrate, and move through the body tissue in the area of the implant 31. The electrical current and metal ion movement has an advantageous bactericidal and germicidal action for the prevention and control of a mastitis condition in the udder.

While there has been shown and described a preferred embodiment of a dispersing instrument, udder implants, and method of placing the implants into a cow's udder, it is understood that changes in the dispensing instrument, udder implants, and method of placing the implants into a cow's udder may be made by those skilled in the art without departing from the invention. The invention is defined in the following Claims.

The embodiments of the invention in which an exclusive property or privilege is claimed are defined as follows:

1. A method of inhibiting mastitis in the udder and teat canal of a bovine animal comprising: locating metallic silver in the udder of a bovine animal, leaving said metallic silver in said udder whereby silver ions originating from said metallic silver provide micro-organism control with the udder, and introducing a sulphur compound into said udder, said sulphur compound reacting with said metallic silver to produce anti-bacterial and anti-virus substances.

2. The method of claim 1 wherein: said core and metallic silver associated therewith are located in the udder cavity adjacent the teat canal.

3. A method of inhibiting mastitis in the udder and teat canal of a bovine animal comprising: locating a metal in the udder of a bovine animal, said metal characterized as being the type that will liberate metal ions that have effective micro-organism control within the udder, leaving said metal in said udder whereby the metal ions originating from said metal control mastitis in the udder, and introducing a sulphur compound in said udder, said sulphur compound reacting with said metal to produce substances that treat mastitis.

4. The method of claim 3 wherein: said core and metal associated therewith are located in the udder cavity adjacent the teat canal.

* * * * *